United States Patent
Wang et al.

(10) Patent No.: US 9,410,897 B2
(45) Date of Patent: Aug. 9, 2016

(54) FILM EDGE DETECTING METHOD AND FILM EDGE DETECTING DEVICE

(71) Applicants: BOE TECHNOLOGY GROUP CO., LTD., Beijing (CN); BEIJING BOE DISPLAY TECHNOLOGY CO., LTD., Beijing (CN)

(72) Inventors: Shoukun Wang, Beijing (CN); Huibin Guo, Beijing (CN); Yuchun Feng, Beijing (CN); Liangliang Li, Beijing (CN); Xiaoxiang Zhang, Beijing (CN); Zongjie Guo, Beijing (CN)

(73) Assignees: BOE Technology Group Co., Ltd., Beijing (CN); Beijing BOE Display Technology Co., Ltd., Beijing (CN)

( * ) Notice: Subject to any disclaimer, the term of this patent is extended or adjusted under 35 U.S.C. 154(b) by 106 days.

(21) Appl. No.: 14/548,997

(22) Filed: Nov. 20, 2014

(65) Prior Publication Data

US 2015/0369748 A1 Dec. 24, 2015

(30) Foreign Application Priority Data

Jun. 24, 2014 (CN) .......................... 2014 1 0287383

(51) Int. Cl.
*G01B 11/14* (2006.01)
*G01N 21/84* (2006.01)
(Continued)

(52) U.S. Cl.
CPC ............ *G01N 21/8422* (2013.01); *G01B 11/00* (2013.01); *G01B 11/24* (2013.01); *G01N 21/8851* (2013.01); *G01N 2201/10* (2013.01)

(58) Field of Classification Search
CPC .......... G01N 21/8422; G01N 2201/10; G01N 21/8851; G01B 11/00

USPC .................. 356/614–625, 630, 237.2–237.6; 250/599.22

See application file for complete search history.

(56) References Cited

U.S. PATENT DOCUMENTS

2004/0063007 A1* 4/2004 Machida ............. G03F 7/70633 430/22
2004/0169869 A1* 9/2004 Shin ................... G01N 21/9501 356/635

(Continued)

FOREIGN PATENT DOCUMENTS

CN 201570490 U 9/2010
CN 201688801 U 12/2010

(Continued)

OTHER PUBLICATIONS

First Office Action issued Jun. 2, 2016, and its English translation in corresponding Chinese Application No. 201410287383.5.

*Primary Examiner* — Tarifur Chowdhury
*Assistant Examiner* — Isiaka Akanbi
(74) *Attorney, Agent, or Firm* — Nath, Goldberg & Meyer; Joshua B. Goldberg

(57) ABSTRACT

The present invention provides a film edge detecting method and a film edge detecting device. The film edge detecting method is used for detecting a film edge of a film layer formed on a substrate, the film layer comprises a patterned film layer, the method includes: forming at least one scale pattern in the patterned film layer, a film edge of the patterned film layer corresponding to an edge of the scale pattern; obtaining a patterned film edge indication value of the edge of the scale pattern; and obtaining a second distance, which is a distance between the film edge of the non-patterned film layer and a corresponding edge of the substrate, based on the non-patterned film edge indication value and a preset reference value of the corresponding edge of the substrate.

13 Claims, 4 Drawing Sheets

(51) Int. Cl.
*G01B 11/00* (2006.01)
*G01N 21/88* (2006.01)
*G01B 11/24* (2006.01)

(56) References Cited

U.S. PATENT DOCUMENTS

| | | | | |
|---|---|---|---|---|
| 2006/0044571 | A1* | 3/2006 | Whitefield | G01N 21/9503 356/625 |
| 2009/0075012 | A1* | 3/2009 | Van Dijk | G03F 7/70775 428/64.4 |
| 2011/0212389 | A1* | 9/2011 | Hirukawa | G03F 1/14 430/5 |
| 2013/0138238 | A1* | 5/2013 | Yang | H01L 21/6715 700/114 |
| 2013/0335751 | A1* | 12/2013 | Hirota | G01B 11/14 356/623 |

FOREIGN PATENT DOCUMENTS

| | | |
|---|---|---|
| CN | 102569113 A | 7/2012 |
| CN | 102607370 A | 7/2012 |
| KR | 101231184 B1 | 2/2013 |

\* cited by examiner

FILM EDGE DETECTING METHOD AND FILM EDGE DETECTING DEVICE

FIELD OF THE INVENTION

The present invention relates to the field of display technology, and in particularly, relates to a film edge detecting method and a film edge detecting device.

BACKGROUND OF THE INVENTION

With the development of the display technology, various display devices have been widely used. The mainstream of the display devices may include: thin film transistor liquid crystal display (TFT-LCD), Active Matrix Organic Light Emitting Diode (AMOLED), and the like.

In the manufacturing processes of various display devices, various structures need to be formed on the substrate. For example, films are deposited on the substrate, and then a patterning process is performed on the films to form various patterns; or only depositing films on the substrate to form film layers. Here, the patterning process may include processes such as photo resist coating, exposure, developing, etching, photo resist stripping, and the like.

In depositing a film and performing a patterning process, substrate shift, mask shift in the exposure process, and etching time variation in the etching process all can result in a variation in distance between the edge of the film and the edge of the substrate. There is no technical solution that can detect the film edge in the prior art, which results in that the variation in the distance between the edge of the film and the edge of the substrate may not be detected in time, thus reducing the yield of the production and increasing the production loss.

SUMMARY OF THE INVENTION

The present invention provides a film edge detecting method and a film edge detecting device, to improve the production yield and reduce the production loss.

To achieve the above object, the present invention provides a film edge detecting method, which is used for detecting a film edge of a film layer formed on a substrate, the film layer comprising a patterned film layer, and the method including steps of:

forming at least one scale pattern in the patterned film layer, a film edge of the patterned film layer corresponding to an edge of the scale pattern;

obtaining a patterned film edge indication value of the edge of the scale pattern; and obtaining a first distance, which is a distance between the edge of the scale pattern and a corresponding edge of the substrate, based on the patterned film edge indication value and a preset reference value of the corresponding edge of the substrate.

When the film edge detecting method is used to detect a film edge of a non-patterned film layer formed above or below the patterned film layer, the method further includes steps of:

obtaining a non-patterned film edge indication value of a film edge of the non-patterned film edge through the scale pattern; and obtaining a second distance, which is a distance between the film edge of the non-patterned film layer and a corresponding edge of the substrate, based on the non-patterned film edge indication value and a preset reference value of the corresponding edge of the substrate.

Optionally, one or more scale patterns are formed corresponding to each edge of the substrate.

Optionally, the patterned film edge indication value is a numerical value, and the step of obtaining a first distance based on the patterned film edge indication value and a preset reference value of the corresponding edge of the substrate includes a step of:

obtaining a difference value by subtracting the reference value from the patterned film edge indication value of the edge of the scale pattern and an absolute value of the difference value is the first distance.

Optionally, the patterned film edge indication value is a two-dimensional code, and the step of obtaining a first distance based on the patterned film edge indication value and a preset reference value of the corresponding edge of the substrate includes steps of:

converting the two-dimensional code into a numerical value; and obtaining a difference value by subtracting the reference value from the converted numerical value, and an absolute value of the difference value is the first distance.

Optionally, the non-patterned film edge indication value is a numerical value, and the step of obtaining the second distance based on the non-patterned film edge indication value and a preset reference value of the corresponding edge of the substrate includes a step of:

obtaining a difference value by subtracting the reference value from the obtained non-patterned film edge indication value of the edge of the non-patterned film layer, and an absolute value of the difference value is the second distance.

Optionally, the non-patterned film edge indication value is a two-dimensional code, and the step of obtaining the second distance based on the non-patterned film edge indication value and a preset reference value of the corresponding edge of the substrate includes steps of:

converting the two-dimensional code into a numerical value; and obtaining a difference value by subtracting the reference value from the converted numerical value, and an absolute value of the difference value is the first distance.

Optionally, the reference value is 0.

The present invention provides a film edge detecting device, which is used for detecting a film edge of a film layer formed on a substrate, the film layer comprising a patterned film layer, wherein, at least one scale pattern is formed in the patterned film layer, a film edge of the patterned film layer corresponds to an edge of the scale pattern, and the film edge detecting device includes:

an obtaining module, which is configured to obtain a patterned film edge indication value of the edge of the scale pattern; and a generating module, which is configured to obtain a first distance, which is a distance between the edge of the scale pattern and a corresponding edge of the substrate, based on the obtained patterned film edge indication value and a preset reference value of the corresponding edge of the substrate.

Optionally, the film layer further comprises a non-patterned film layer formed above or below the patterned film layer, wherein, the obtaining module obtains a non-patterned film edge indication value of an edge of the non-patterned film layer through the scale pattern; and the generating module obtains the second distance, which is a distance between the edge of the non-patterned film layer edge and a corresponding edge of the substrate, based on the non-patterned film edge indication value obtained by the obtaining module and the reference value of the corresponding edge of the substrate.

Optionally, when the patterned film edge indication value is a numerical value, the obtaining module comprises a micro measurement device; and when the patterned film edge indication value is a two-dimensional code, the obtaining module comprises a scanning device.

Optionally, when the non-patterned film edge indication value is a numerical value, the obtaining module comprises a micro measurement device; and when the non-patterned film edge indication value is a two-dimensional code, the obtaining module comprises a scanning device.

The beneficial effects of the present invention:

In the film edge detecting method and the film edge detecting device according to the present invention, a patterned film edge indication value of an edge of a scale pattern is obtained, and then a first distance is obtained based on the patterned film edge indication value and a preset value of a substrate edge; and/or a non-patterned film edge indication value of an edge of a non-patterned film layer is obtained through a scale pattern which is above or below the non-patterned film layer, and then a second distance d2 is obtained based on the non-patterned film edge indication value and a preset reference value of the substrate edge. The present invention can detect a film edge in the manufacturing process, so as to detect a variation in the distance between a film edge and a substrate edge in time during the manufacturing process, thereby improving the production yield and reducing the production loss.

DETAILED DESCRIPTION OF THE EMBODIMENTS

In order to enable a person skilled in the art to better understand the technical solutions of the present invention, a film edge detecting method and a film edge detecting device will be described in more details below in conjunction with the accompanying drawings.

Embodiment 1

Embodiment 1 of the present invention provides a film edge detecting method, which is used for detecting a film edge of a patterned film layer above a substrate. Therefore, before detecting the film edge of the patterned film layer, the following steps 100a and 100b need to be performed in advance. It should be noted that the term "patterned film layer" indicates a film layer capable of forming a pattern therein.

Step 100a includes: forming a patterned film layer on a substrate.

Figure 1A:
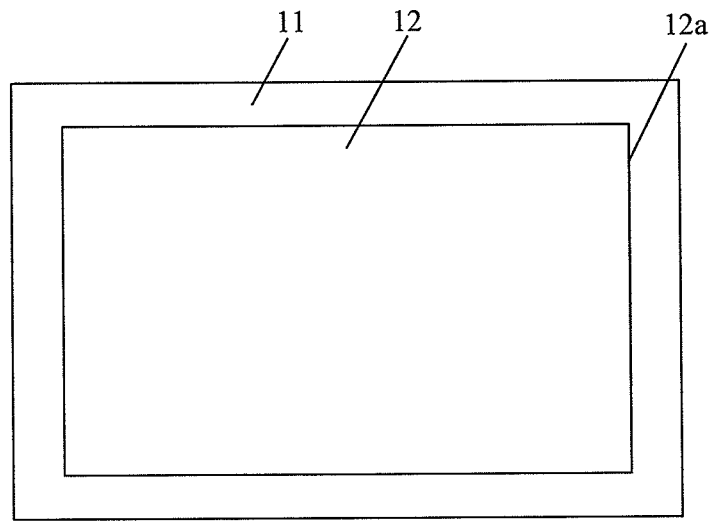
FIG. 1a is a schematic diagram of forming a patterned film layer in Embodiment 1 of the present invention.

FIG. 1 is a schematic diagram of forming a patterned film layer in Embodiment 1 of the present invention. As shown in FIG. 1a, a patterned film layer 12 is deposited on the substrate 11. Due to the requirement of the manufacturing process, the patterned film layer 12 does not completely cover the substrate 11, and therefore a certain distance exists between a film edge 12a of the patterned film layer 12 and a corresponding edge of the substrate 11. From FIG. 1a, it can be seen that the patterned film layer 12 comprises four film edges, and distances exist between the respective film edges and the edges of the substrate 11 corresponding thereto, and these distances maybe identical or different.

Step 100b includes: performing a patterning process on the patterned film layer to form a structure pattern and at least one scale pattern, a film edge of the patterned film layer corresponding to an edge of the scale pattern.

Figure 1B:
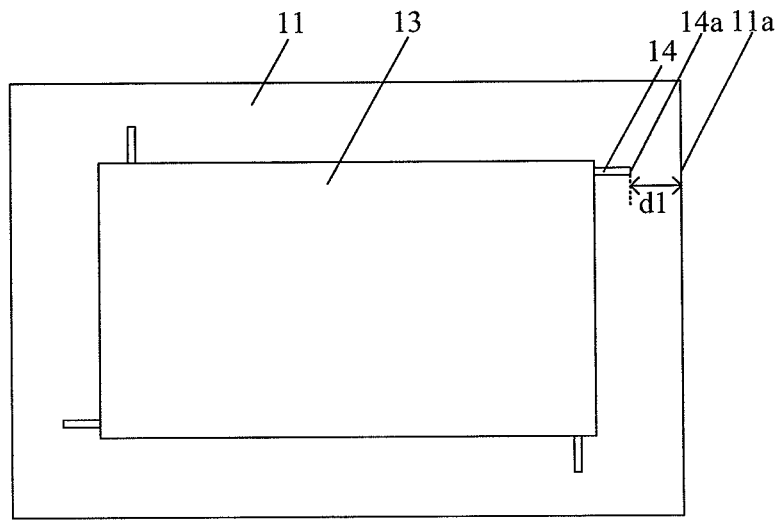
FIG. 1b is a schematic diagram of forming a structure pattern and a scale pattern in Embodiment 1 of the present invention.

FIG. 1b is a schematic diagram of forming a structure pattern and a scale pattern in Embodiment 1 of the present invention. As shown in FIG. 1b, a patterning process is performed on the patterned film layer 12 to form a structure pattern 13 and at least one scale pattern 14. The structure pattern 13 may be designed to be a pattern with various structures, for example, if the patterned film layer is a gate metal layer, the structure pattern 13 may include patterns of gate lines and gates; if the patterned film layer is a source/drain metal layer, the structure pattern 13 may include patterns of data lines, sources and drains. The specific structure of the structure pattern 13 is not shown in FIG. 1b. In the present embodiment, the scale pattern 14 has marks capable of indicating length, each mark corresponds to one indication value (hereinafter referred to as patterned film edge indication value), and the unit of the marks, as well as the length of the scale pattern 14, can be set based on an actual requirement. For example, the length of the scale pattern 14 may be larger than 0 mm but less than or equal to 30 mm. The scale pattern 14 and structure pattern 13 are disposed in the same layer. A film edge 12a of the patterned film layer 12 (as shown in FIG. 1a) is used for forming a scale pattern edge 14 (as shown in FIG. 1b) of the scale pattern. That is, the film edge 12a of the patterned film layer 12 corresponds to the scale pattern edge 14a of the scale pattern 14, and therefore, in the present embodiment, the film edge 12a of the patterned film layer 12 can be determined by detecting the scale pattern edge 14a of the scale pattern 14. Each edge of the substrate may correspond to one or more scale patterns 14. In FIG. 1b, description is given by taking a case that four pattern scales 14 are formed and each edge of the substrate corresponds to one pattern scale 14 as an example.

Figure 2:
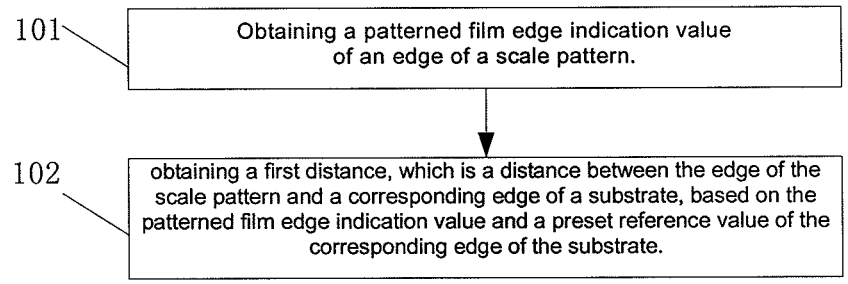
FIG. 2 is a flowchart of a film edge detecting method provided by Embodiment 1 of the present invention.

FIG. 2 is a flowchart of a film edge detecting method provided by Embodiment 1 of the present invention, as shown in FIG. 2, the film edge detecting method includes steps 101 and 102.

Step 101 includes: obtaining a patterned film edge indication value at an edge of the scale pattern.

Figure 3A:
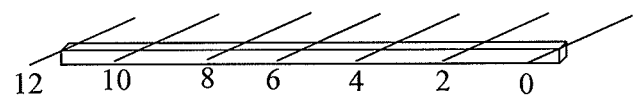
FIG. 3a is a schematic diagram of a standard structure of the scale pattern in Embodiment 1 when patterned film edge indication value is a numerical value.
Figure 3B:
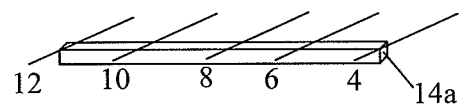
FIG. 3b is a schematic diagram of an actual structure of the scale pattern when patterned film edge indication value in FIG. 1b is a numerical value.

In the present embodiment, the scale patterns 14 may be categorized into two types according to the type of the marks:

In the first type, the patterned film edge indication value is numerical value. FIG. 3a is a schematic diagram of a standard structure of a scale pattern 14 when the patterned film edge indication value is numerical value in Embodiment 1. As shown in FIG. 3a, a complete scale pattern may be formed in an ideal situation, and the scale pattern edge 14a of the complete scale pattern is right on and coincides with the substrate edge 11a of the substrate 11. For example, a start value and a stop value of the patterned film edge indication values on the complete scale pattern is 0 and 12, respectively, and the start value is located at a position where the substrate edge 11a is located. To form the complete scale pattern, the patterned film layer 12 needs to completely cover the substrate 11, i.e., there is no distance between the film edge 12a of the patterned film layer 12 and the corresponding substrate edge 11a of the substrate 11. However, the patterned film layer 12, due to the influence by the process design and the actual technological process, may not completely cover the substrate 11, and therefore, the complete scale pattern may not be formed in an actual application. But, it should be noted that the technical solution of the present invention should also include a solution in which the complete scale pattern is formed (i.e., the distance between the film edge 12a of the patterned film layer 12 and the corresponding substrate edge 11a of the substrate 11 is 0). FIG. 3b is a schematic diagram of an actual structure of the scale pattern according to the Embodiment 1 of the present invention when the patterned film edge indication value in the FIG. 1b is numerical value. As shown in FIG. 3b, the patterned film edge indication value at the scale pattern edge 14a of the scale pattern 14 formed in the step 100b is 4. Specifically, the value at the edge of the scale can be obtained by visual observation when the patterned film edge indication value is numerical value.

Figure 3C:
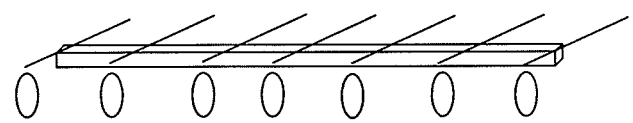
FIG. 3c is a schematic diagram of a standard structure of the scale pattern in Embodiment 1 when patterned film edge indication value is a two-dimensional code.
Figure 3D:
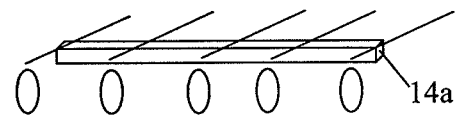
FIG. 3d is a schematic diagram of an actual structure of the scale pattern when patterned film edge indication value in the FIG. 1b is a two-dimensional code.

In the second type, the patterned film edge indication value is two-dimensional code. FIG. 3c is a schematic diagram of a standard structure of a scale pattern 14 when the patterned film edge indication value is two-dimensional code in Embodiment 1. As shown in the FIG. 3c, a complete scale pattern may be formed in an ideal situation, and the scale pattern edge 14a of the complete scale pattern is right on and coincides with the substrate edge 11a of the substrate 11. For example, a start two-dimensional code on the complete scale pattern 14 is located at a position where the substrate edge 11a is located. It should be noted that the two-dimensional codes in FIG. 3c are represented by oval symbols without showing their contents. To form the complete scale pattern, the patterned film layer 12 needs to completely cover the substrate 11, i.e., there is no distance between the film edge 12a of the patterned film layer 12 and the corresponding substrate edge 11a of the substrate 11. However, the patterned film layer 12, due to influence by the process design and the actual technological process, may not completely cover the substrate 11, and therefore, the complete scale pattern cannot be formed in an actual application. FIG. 3d is a schematic diagram of an actual structure of the scale pattern according to Embodiment 1 of the present invention when the patterned film edge indication value in FIG. 1b is two-dimensional code. As shown in the FIG. 3d, the patterned film edge indication value at the scale pattern edge 14a of the scale pattern 14 formed in the step 100b is a two-dimensional code. Specifically, the two-dimensional code at the scale pattern edge can be obtained by a scanning device when the patterned film edge indication value is two-dimensional code.

Step 102 includes: obtaining a first distance d1, which is a distance between a scale pattern edge and a corresponding edge of the substrate, based on a patterned film edge indication value at the scale pattern edge and a preset reference value of a corresponding substrate edge.

As shown in FIG. 1b, the first distance d1 is the distance between the scale pattern edge 14a and the corresponding substrate edge 11a. The scale pattern edge 14a corresponds to the film edge 12a of the patterned film layer 12, and therefore, the first distance d1 is also a distance between the film edge 12a of the patterned film layer 12 and the corresponding substrate edge 11a.

If the patterned film edge indication value is numerical value, the step 102 specifically includes: obtaining a difference value by subtracting the reference value from the patterned film edge indication value (numerical value), and an absolute value of the difference value is the first distance d1. For example, when the indication value is 4 and the reference value is 0, the difference value is 4, and therefore, the first distance d1 is 4. Preferably, the reference value is 0, so the patterned film edge indication value at the scale pattern edge 14a is the first distance d1, and in this case, the first distance d1 can be obtained directly by reading the patterned film edge indication value at the scale pattern edge 14a.

If the patterned film edge indication value is two-dimensional code, the two-dimensional code may be converted into numerical value first, and then the first distance d1 is obtained by using the above specific method in the step 102 when the patterned film edge indication value is numerical value, and the specific process is not repeated.

In the technical solution of the film edge detecting method according to the present embodiment, a patterned film edge indication value at a scale pattern edge is first obtained, and then a first distance can be obtained based on the patterned film edge indication value and a preset reference value of a corresponding edge of the substrate. The present embodiment can detect a film edge in the manufacturing process, so as to detect a variation in the distance between the film edge and the substrate edge in time during the manufacturing process, and thus improving the production yield and reducing the production loss.

Embodiment 2

Embodiment 2 of the present invention provides a film edge detecting method, which is used for detecting a film edge of a non-patterned film layer above a substrate. The non-patterned film layer may be above or below the scale pattern. The present embodiment is described by taking a case that the non-patterned film layer is above the scale pattern as an example, that is to say, the non-patterned film layer is above the structure pattern and the scale pattern. Therefore, before detecting the edge of the non-patterned film layer, the following steps 200a to 200c need to be performed in advance. It should be noted that the term "patterned film layer" indicates a film layer incapable of forming a pattern therein.

Step 200a includes: forming a patterned film layer on a substrate.

The detailed description of this step refers to that described in the step 100a of Embodiment 1.

Step 200b includes: performing a patterning process on the patterned film layer to form a structure pattern and at least one scale pattern, a film edge of the patterned film layer corresponds to an edge of the scale pattern.

The detailed description of this step refers to that described in the step 100b of Embodiment 1.

Step 200c includes: forming a non-patterned film layer on the structure pattern and the scale pattern.

Figure 4:
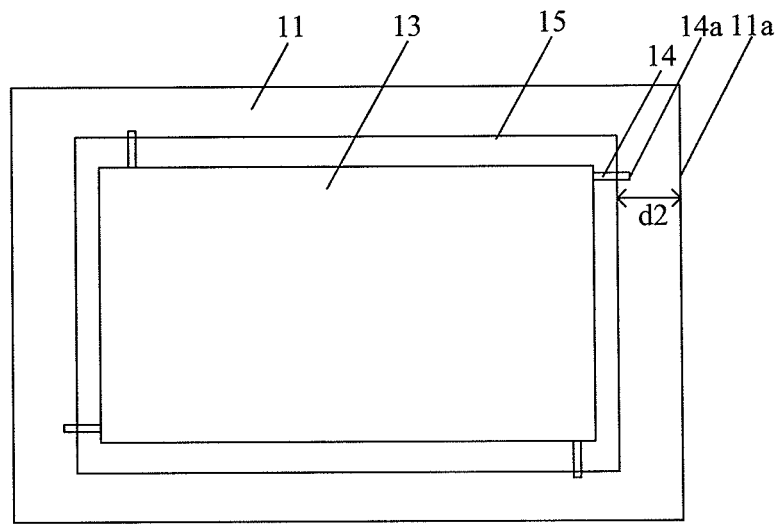
FIG. 4 is a schematic diagram of forming a non-patterned film layer in Embodiment 1.

FIG. 4 is a schematic diagram of forming a non-patterned film layer in Embodiment 2. As shown in FIG. 4, a non-patterned film layer 15 is deposited on the structure pattern 13 and the scale pattern 14. Due to a high transmittance of the non-patterned film layer 15, the specific structure of the scale pattern can hardly be observed by human eyes or detected by a device if the scale pattern is formed in the non-patterned film layer 15 and therefore, in the present invention, the scale pattern is not formed in the non-patterned film layer, but a film edge may be detected by using the scale pattern located under the non-patterned film layer. Generally, a material of the non-patterned film layer 15 is a nonmetal material.

Figure 5:
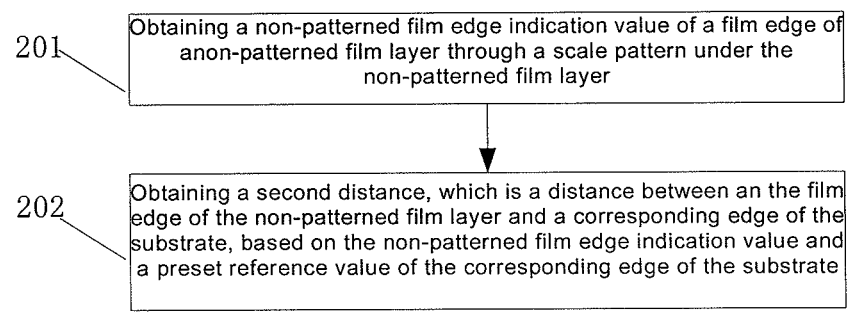
FIG. 5 is a flowchart of a film edge detecting method provided by Embodiment 2 of the present inventions.

FIG. 5 is a flowchart of a film edge detecting method provided by Embodiment 2 of the present invention. As shown in FIG. 5, the film edge detecting method may include steps 201 and 202:

Step 201: obtaining an indication value at an edge of the non-patterned film layer 15 (also referred to as non-patterned film edge indication value) through the scale pattern 14 located under the non-patterned film layer 15.

Figure 6:
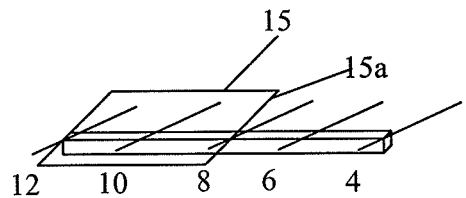
FIG. 6 is schematic diagram of detecting a film edge of the non-patterned film layer shown in FIG. 4.

FIG. 6 is schematic diagram of detecting a film edge of the non-patterned film layer in FIG. 4. As shown in FIGS. 4 and 6, the non-patterned film edge indication value of the non-patterned film layer edge 15a is obtained through the scale pattern 14 located under the non-patterned film layer 15. The non-patterned film edge indication value in FIG. 6 is numerical value, for example, the non-patterned film edge indication value of the non-patterned film layer edge 15a is 8. Alternatively, the non-patterned film edge indication value may be two-dimensional code, and this condition is not shown.

When the patterned film edge indication value is numerical value, in this step, the value at the edge 15a of the non-patterned film layer 15 may be obtained from the value of the scale pattern 14 under the non-patterned film layer 15 by visual observation. Since the non-patterned film layer is a nonmetal material layer with a certain transmittance, when the scale pattern 14 is under the non-patterned film layer 15, the scale pattern 14 can be observed through the non-patterned film layer 15. Since the non-patterned film layer 15 is not totally transparent, the color of the non-patterned film layer 15 is different from the color of a surrounding region in which no non-patterned film layer 15 is formed, so that the film edge 15a of the non-patterned film layer 15 can be directly observed and the patterned film edge indication value on the scale pattern 14 corresponding to said film edge can be read. In an actual application, if the non-patterned film layer 15 is under the scale pattern 14, the film edge 15a of the non-patterned film layer can be observed and the patterned film edge indication value on the scale pattern 14 corresponding to said film edge can be read by a micro-measurement device such as a magnifying glass or a microscope.

When the patterned film edge indication value is two-dimensional code, this step may specifically include scanning the two-dimensional code on the scale pattern 14 under the non-patterned film layer 15 by a scanning device. The scanning device emits light to the non-patterned film 15, as the intensities of the reflected lights formed in the non-patterned film layer 15 and a region in which no non-patterned film layer 15 is formed are different, the scanning device can detect the position of the film edge 15a of the non-patterned film layer 15 based on the received intensity of the reflected light, the scanning device then moves to the position where the film edge 15a of the non-patterned film layer 15 is located and scans the two-dimensional code corresponding to the film edge 15a of the non-patterned film layer 15.

Step 202 includes: obtaining a second distance d2, which is a distance between a non-patterned film layer edge 15a and a corresponding substrate edge 11a, based on the non-patterned film edge indication value and a preset reference value of the substrate edge.

As shown in FIGS. 4 and 6, the second distance d2 is the distance between the non-patterned film layer edge 15a and the substrate edge 11a corresponding thereto.

If the patterned film edge indication value is numerical value, the step 104 particularly includes: obtaining a difference value by subtracting the reference value from the obtained value at the film edge 15a of the non-patterned film layer 15, and an absolute value of the difference value is the second distance d2. As shown in FIG. 6, when the value at the film edge 15a of the non-patterned film layer 15 is 8 and the reference value is 0, the different value is 8, and therefore, the second distance d2 is 8. Preferably, the reference value is 0, so the value corresponding to the film edge 15a of the non-patterned film layer 15 is the second distance d2, and in this case, the second distance d2 can be directly obtained by reading the non-patterned film edge indication value at the film edge 15a of the non-patterned film layer 15.

If the patterned film edge indication value is two-dimensional code, the two-dimensional code maybe converted into numerical value, and then the second distance d2 is obtained by using the above specific method in the step 202 when the patterned film edge indication value is numerical value, and the specific process is not repeated. In the technical solution of the film edge detecting method provided by the present embodiment, a non-patterned film edge indication value at an edge of a non-patterned film layer can be first obtained through a scale pattern which is above or below the non-patterned film layer, and then a second distance d2 can be obtained based on the obtained non-patterned film edge indication value and a preset reference value of a substrate edge. The present embodiment can detect a film edge in the manufacturing process, so as to detect a variation in the distance between the film edge and the substrate edge in time during the manufacturing process, thus improving the production yield and reducing the production loss.

Embodiment 3

Embodiment 3 of the present invention provides a film edge detecting method, which is used for detecting a film edge of a non-patterned film layer on a substrate. Before detecting an edge of a non-patterned film layers, the following steps 300a to 300b need to be performed in advance.

Step 300a includes: forming a patterned film layer on a substrate.

The detailed description of this step refers to that described in the step 100a of Embodiment 1.

Step 300b includes: performing a patterning process on the patterned film layer to form a structure pattern and at least one scale pattern, a film edge of the patterned film layer corresponds to an edge of the scale pattern.

The detailed description of this step refers to that described in the step 100b of Embodiment 1.

Figure 7:
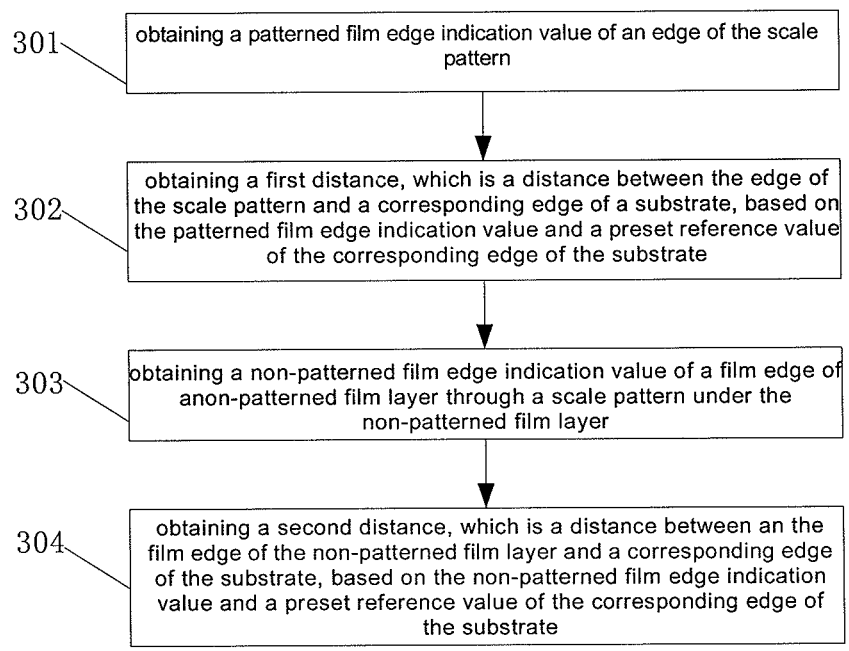
FIG. 7 is a flowchart of a film edge detecting method provided by Embodiment 3 of the present invention.

FIG. 7 is a flowchart of a film edge detecting method provided by Embodiment 3 of the present invention, as shown in FIG. 7, the film edge detecting method includes steps 301 to 304.

Step 301 includes: obtaining a patterned film edge indication value of an edge of the scale pattern edge.

The detailed description of this step refers to that described in the step 101 of Embodiment 1.

Step 302 includes: obtaining a first distance, which is a distance between a film edge of the patterned film layer and a corresponding edge of the substrate, based on the obtained patterned film edge indication value at the edge of the scale pattern and a preset reference value of the substrate edge.

The detailed description of this step refers to that described in the step 102 of Embodiment 1.

At this point, the detection of a film edge of the patterned film layer is completed. Then, a film edge of anon-patterned film layer is detected. Before detecting an edge of the non-patterned film layers, the following step 300c needs to be performed in advance:

Step 300c includes: forming a non-patterned film layer on the structure pattern and the scale pattern.

The detailed description of this step refers to that described in the step 200c of Embodiment 2.

This film edge detecting method further includes steps 303 and 304.

Step 303: obtaining a non-patterned film edge indication value at a film edge of the non-patterned film layer through the scale pattern under the non-patterned film layer.

The detailed description of this step refers to that described in the step 201 of Embodiment 2.

Step 304: obtaining a second distance, which is the distance between a film edge of the non-patterned film layer and the corresponding substrate edge, based on the obtained non-patterned film edge indication value and a preset reference value of the substrate edge.

The detailed description of this step refers to that described in the step 202 of Embodiment 2.

It should be noted that, the patterned film layer in the present invention refers to a film layer that can form a scale pattern, and preferably, the patterned film layer may be a metal film layer, such as a gate metal layer, or a source-drain metal layer; the non-patterned film layer refers to a film layer that cannot form a scale pattern, and preferably, the non-patterned film layer may be a nonmetal film layer, such as a pixel electrode layer or an insulating layer.

In the technical solution of the film edge detecting method according to the present embodiment, a patterned film edge indication value at an edge of a scale pattern is obtained, and then a first distance is obtained based on the obtained patterned film edge indication value and a preset reference value of a substrate edge; and/or a non-patterned film edge indication value of an edge of a non-patterned film layer edge is obtained through the scale pattern which is above or below the non-patterned film layer, and then a second distance d2 is obtained based on the obtained non-patterned film edge indication value and a preset reference value of the substrate edge. The present embodiment can detect a film edge in the manufacturing process, so as to detect a variation in the distance between a film edge and a substrate edge in time during the manufacturing process, thus improving the production yield and reducing the production loss.

Embodiment 4

Figure 8:
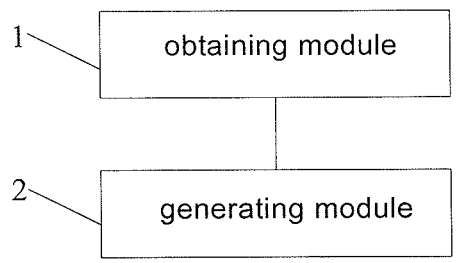
FIG. 8 is a schematic diagram of a structure of a film edge detecting device provided by Embodiment 4 of the present invention.

Embodiment 4 of the present invention provides a film edge detecting device, which is used to detect a film edge of a patterned film layer and/or a non-patterned film layer on the substrate, the patterned film layer is used for forming a structure pattern and at least one scale pattern, a film edge of the patterned film layer corresponds to an edge of the scale pattern. FIG. 8 is a schematic diagram of a structure of a film edge detecting device provided by the Embodiment 4 of the present invention. As shown in FIG. 8, the film edge detecting device includes: an obtaining module 1 and a generating module 2.

When the film edge detecting device is used to detect a film edge of a patterned film layer, the obtaining module 1 obtains a patterned film edge indication value at an edge of the scale pattern; the generating module 2 obtains a first distance, which is a distance between the edge of the scale pattern and a corresponding edge of the substrate, based on the patterned film edge indication value at the edge of the scale pattern obtained by the obtaining module 1 and a preset reference value of the substrate edge.

The film edge detecting device is also used for detecting a film edge of a non-patterned film layer. At this time, the obtaining module 1 obtains a non-patterned film edge indication value of an edge of the non-patterned film layer through a scale pattern above or below the non-patterned film layer; the generating module 2 obtains a second distance, which is a distance between the edge of the non-patterned film layer and a corresponding edge of the substrate, based on the non-patterned film edge indication value of the edge of the non-patterned film layer obtained by the obtaining module 1 and a preset reference value of the substrate edge.

Preferably, the obtaining module 1 comprises a micro-measurement device when the patterned film edge indication value is numerical value; and the obtaining module 1 comprises a scanning device when the patterned film edge indication value is two-dimensional code. Preferably, the micro-measurement device may be a magnifying glass or a microscope. Preferably, the scanning device can be a device that can emit light, receive reflected light and scan a two-dimensional code. Optionally, the scanning device may not has a function of emitting light and receiving reflected light when ambient light is strong enough, and therefore, the scanning device may be a device that can only scan a two-dimensional code.

The film edge detecting device provided by the present embodiment can be used to perform the film edge detecting method provided by Embodiment 1, Embodiment 2 or Embodiment 3, the detailed description thereof may refer to that described in Embodiment 1, Embodiment 2 or Embodiment 3, and is not repeated here.

In the technical solution of the film detecting device according to the present embodiment, a patterned film edge indication value at an edge of a scale pattern is obtained, and a first distance is obtained based on the obtained patterned film edge indication value and a preset reference value of a corresponding edge of the substrate. The present embodiment can detect a film edge in the manufacturing process, so as to detect a variation in the distance between the film edge and the substrate edge in time during the manufacturing process, thus improving the production yield and reducing the production loss.

It should be understood that, the above implementations are only exemplary embodiments for the purpose of explaining the principle of the present invention, and the present invention is not limited thereto. For a person skilled in the art, various improvements and modifications may be made to the present invention without departing from the spirit and essence of the present invention. These improvements and modifications are also deemed as the protection scope of the present invention.

What is claimed is:

1. A film edge detecting method, which is used for detecting a film edge of a film layer formed on a substrate, the film layer comprising a patterned film layer, and the method including steps of:
   forming at least one scale pattern in the patterned film layer, a film edge of the patterned film layer corresponding to an edge of the scale pattern;
   obtaining a patterned film edge indication value of the edge of the scale pattern; and
   obtaining a first distance, which is a distance between the edge of the scale pattern and a corresponding edge of the substrate, based on the patterned film edge indication value and a preset reference value of the corresponding edge of the substrate.

2. The film edge detecting method according to claim 1, the film layer further comprises a non-patterned film layer formed above or under the patterned film layer, the method further includes steps of:
   obtaining a non-patterned film edge indication value of a film edge of the non-patterned film through the scale pattern; and
   obtaining a second distance, which is a distance between the film edge of the non-patterned film layer and a corresponding edge of the substrate, based on the non-patterned film edge indication value and a preset reference value of the corresponding edge of the substrate.

3. The film edge detecting method according to claim 1, wherein one or more scale pattern is formed corresponding to each edge of the substrate.

4. The film edge detecting method according to claim 1, wherein, the patterned film edge indication value is a numerical value, the step of obtaining a first distance based on the patterned film edge indication value and a preset reference value of the corresponding edge of the substrate includes a step of:
   obtaining a difference value by subtracting the reference value from the patterned film edge indication value of the edge of the scale pattern, and an absolute value of the difference value is the first distance.

5. The film edge detecting method according to claim 1, wherein, the patterned film edge indication value is a two-dimensional code, and the step of obtaining a first distance based on the patterned film edge indication value and a preset reference value of the corresponding edge of the substrate includes steps of:
   converting the two-dimensional code corresponding to the patterned film edge indication value of the edge of the scale pattern into a numerical value; and
   obtaining a difference value by subtracting the reference value from the converted numerical value, and an absolute value of the difference value is the first distance.

6. The film edge detecting method according to claim 2, wherein, the non-patterned film edge indication value is a numerical value, the step of obtaining the second distance based on the non-patterned film edge indication value and a preset reference value of the corresponding edge of the substrate includes a step of:
   obtaining a difference value by subtracting the reference value from the non-patterned film edge indication value of the edge of the non-patterned film layer, and an absolute value of the difference value is the second distance.

7. The film edge detecting method according to claim 2, wherein, the non-patterned film edge indication value is two-dimensional code, the step of obtaining the second distance based on the non-patterned film edge indication value and a preset reference value of the corresponding edge of the substrate includes steps of:
   converting the two-dimensional code corresponding to the non-patterned film edge indication value of the edge of the non-patterned film layer into a numerical value; and
   obtaining a difference value by subtracting the reference value from the converted numerical value, and an absolute value of the difference value is the second distance.

8. The film edge detecting method according to claim 1, wherein the reference value is 0.

9. The film edge detecting method according to claim 2, wherein the reference value is 0.

10. A film edge detecting device, which is used for detecting a film edge of a film layer formed on a substrate, the film layer comprising a patterned film layer, wherein at least one scale pattern is formed in the patterned film layer, and a film edge of the patterned film layer corresponds to an edge of the scale pattern, and the film edge detecting device includes:
    an obtaining module, which is configured to obtain a patterned film edge indication value of the edge of the scale pattern; and
    a generating module, which is configured to obtain a first distance, which is a distance between the edge of the scale pattern and a corresponding edge of the substrate, based on the obtained patterned film edge indication value and a preset reference value of the corresponding edge of the substrate.

11. The film edge detecting device according to claim 10, the film layer further comprising a non-patterned film layer formed above or below the patterned film layer, wherein,
    the obtaining module obtains a non-patterned film edge indication value of a film edge of the non-patterned film layer through the scale pattern; and
    the generating module obtains the second distance, which is a distance between the edge of the non-patterned film layer edge and a corresponding edge of the substrate, based on the non-patterned film edge indication value and the reference value of the edge of the substrate.

12. The film edge detecting device according to claim 10, wherein,
    when the patterned film edge indication value is a numerical value, the obtaining module comprises a micro measurement device; and
    when the patterned film edge indication value is a two-dimensional code, the obtaining module comprises a scanning device.

13. The film edge detecting device according to claim 11, wherein,
    when the non-patterned film edge indication value is a numerical value, the obtaining module comprises a micro measurement device; and
    when the non-patterned film edge indication value is a two-dimensional code, the obtaining module comprises a scanning device.

* * * * *